(12) United States Patent
Fattinger

(10) Patent No.: US 10,156,524 B2
(45) Date of Patent: Dec. 18, 2018

(54) DEVICE FOR USE IN THE DETECTION OF BINDING AFFINITIES

(71) Applicant: Hoffmann-La Roche Inc., Nutley, NJ (US)

(72) Inventor: Christof Fattinger, Blauen (CH)

(73) Assignee: Hoffmann-La-Roche Inc., Nutley, NJ (US)

( * ) Notice: Subject to any disclaimer, the term of this patent is extended or adjusted under 35 U.S.C. 154(b) by 0 days.

(21) Appl. No.: 14/646,354

(22) PCT Filed: Dec. 3, 2013

(86) PCT No.: PCT/EP2013/075408
§ 371 (c)(1),
(2) Date: May 20, 2015

(87) PCT Pub. No.: WO2014/086789
PCT Pub. Date: Jun. 12, 2014

(65) Prior Publication Data
US 2015/0276612 A1    Oct. 1, 2015

(30) Foreign Application Priority Data
Dec. 4, 2012  (EP) .................................... 12195532

(51) Int. Cl.
*G01N 33/543* (2006.01)
*G01N 21/77* (2006.01)
(Continued)

(52) U.S. Cl.
CPC ........... *G01N 21/75* (2013.01); *G01N 21/552* (2013.01); *G01N 21/774* (2013.01);
(Continued)

(58) Field of Classification Search
None
See application file for complete search history.

(56) References Cited

U.S. PATENT DOCUMENTS

| 4,815,843 A | 3/1989 | Tiefenthaler et al. |
| 5,071,248 A | 12/1991 | Tiefenthaler et al. |

(Continued)

FOREIGN PATENT DOCUMENTS

| EP | 0000810 B1 | 2/1979 |
| GB | 2342440 A | 4/2000 |

(Continued)

OTHER PUBLICATIONS

Written Opinion of the International Search Authority for International Search Report issued in PCT/EP2013/075408 dated Feb. 3, 2014.

(Continued)

*Primary Examiner* — Neil N Turk
(74) *Attorney, Agent, or Firm* — Mintz Levin Cohn Ferris Glovsky and Popeo, P.C.

(57) ABSTRACT

A device for use in the detection of binding affinities, the device comprising a planar waveguide (2) arranged on a substrate (3), and further comprising an optical coupler (41) having a predetermined length for coupling coherent light (1) of a predetermined wavelength into the planar waveguide (2) such that a parallel beam of coherent light propagates through the planar waveguide (2) with an evanescent field (11) of the coherent light propagating along an outer surface (21) of the planar waveguide (2). The outer surface (21) of the planar waveguide (2) comprises binding sites thereon capable of binding target samples to the binding sites such that light of the evanescent field (11) is diffracted by target samples bound to the binding sites. The binding sites are arranged along a plurality of predetermined straight lines (7) running parallel to one another with a constant distance between adjacent straight lines.

11 Claims, 6 Drawing Sheets

(51) Int. Cl.
*G01N 21/75* (2006.01)
*G01N 21/552* (2014.01)
*G01N 21/55* (2014.01)

(52) U.S. Cl.
CPC ... *G01N 33/54373* (2013.01); *G01N 21/7703* (2013.01); *G01N 2021/752* (2013.01); *G01N 2021/7776* (2013.01); *G01N 2021/7793* (2013.01); *G01N 2201/0438* (2013.01)

(56) References Cited

U.S. PATENT DOCUMENTS

| | | | |
|---|---|---|---|
| 5,455,178 A * | 10/1995 | Fattinger | G01N 21/7743 385/12 |
| 5,738,825 A | 4/1998 | Rudigier et al. | |
| 5,843,651 A | 12/1998 | Stimpson et al. | |
| 6,052,213 A | 4/2000 | Burt et al. | |
| 7,008,794 B2 | 3/2006 | Goh et al. | |
| 7,505,641 B1 | 3/2009 | Senturia et al. | |
| 8,570,509 B2 | 10/2013 | Amako et al. | |
| 8,753,872 B2 | 6/2014 | Goh et al. | |
| 2002/0025534 A1 | 2/2002 | Goh et al. | |
| 2004/0170356 A1 | 9/2004 | Iazikov et al. | |
| 2004/0212890 A1 | 10/2004 | Shiozaki et al. | |
| 2006/0194345 A1 | 8/2006 | Uchiyama et al. | |

FOREIGN PATENT DOCUMENTS

| | | |
|---|---|---|
| JP | 54-34846 | 3/1979 |
| JP | 8-504955 | 5/1996 |
| JP | 9-61346 | 3/1997 |
| JP | 10-506190 | 6/1998 |
| JP | 2000-508083 | 6/2000 |
| JP | 2011-237374 | 11/2001 |
| JP | 2003-528311 | 9/2003 |
| WO | WO 95/03538 | 2/1995 |
| WO | WO 96/09532 | 3/1996 |
| WO | WO 97/36198 | 10/1997 |
| WO | WO 01/71322 A2 | 9/2001 |
| WO | WO 2009/083884 A1 | 7/2009 |

OTHER PUBLICATIONS

International Search Report issued in PCT/EP2013/075408 dated Feb. 3, 2014.
M. Pawlak et al. "Zeptosens' protein microarrays: A novel high performance microarray platform for low abundance protein analysis." Proteomics. vol. 2 (2002): 383-393.
English Abstract of JP1-506190A, dated Jun. 16, 1998, (29 pgs.).
English Abstract of JP09061346A, dated Mar. 7, 1997, (13 pgs.).
English Abstract of JP2000508083A, dated Jun. 27, 2000, (11 pgs.).
English Abstract of JP2011237374A, dated Nov. 24, 2011, (14 pgs.).
English Abstract of JP54034846A, dated Mar. 14, 1979, (2 pgs.).
English Abstract of JP08504955A, dated May 28, 1996 (11 pgs.).
English Abstract of JP2003528311A, dated Sep. 24, 2003, (25 pgs).

\* cited by examiner

DEVICE FOR USE IN THE DETECTION OF BINDING AFFINITIES

RELATED APPLICATION

This application is a national stage application, filed under 35 U.S.C. § 371, of International Application No. PCT/EP2013/075408 filed on Dec. 3, 2013, which claims priority to European Patent Application No. 12195532.2 filed on Dec. 4, 2012, the contents of which are hereby fully incorporated by reference.

The present invention relates to a device for use in the detection of binding affinities as well as a system for the detection of binding affinities in accordance with the respective independent claim.

Such devices are used, for example, as biosensors in a large variety of applications. One particular application is the detection or monitoring of binding affinities or processes. For example, with the aid of such biosensors various assays detecting the binding of target samples to binding sites can be performed. Typically, large numbers of such assays are performed on a biosensor at spots which are arranged in a two-dimensional microarray on the surface of the biosensor. The use of microarrays provides a tool for the simultaneous detection of the binding affinities or processes of different target samples in high-throughput screenings, wherein large numbers of target samples like molecules, proteins or DNA can be analysed quickly. For detecting the affinities of target samples to bind to specific binding sites (e.g. the affinities of target molecules to bind to different capture molecules), a large number of binding sites are immobilised on the surface of the biosensor at spots which can be applied, for instance, by ink-jet spotting or photolithography. Each spot forms an individual measurement zone for a predetermined type of capture molecules. The affinity of a target sample to a specific type of capture molecules is detected and is used to provide information on the binding affinity of the target sample.

A known technique for detecting binding affinities of target samples uses labels which are capable of emitting fluorescent light upon excitation. For example, fluorescent tags can be used as labels for labelling the target samples. Upon excitation, the fluorescent tags are caused to emit fluorescent light having a characteristic emission spectrum. The detection of this characteristic emission spectrum at a particular spot indicates that the labelled target molecule has bound to the particular type of binding sites present at the respective spot.

A sensor for detecting labelled target samples is described in the article "Zeptosens' protein microarrays: A novel high performance microarray platform for low abundance protein analysis", Proteomics 2002, 2, S. 383-393, Wiley-VCH Verlag GmbH, 69451 Weinheim, Germany. The sensor described there comprises a planar waveguide arranged on a substrate, and a grating for coupling coherent light of a predetermined wavelength into the planar waveguide. A further grating is arranged at that end of the planar waveguide remote from the grating for coupling the light into the waveguide. Coherent light that has propagated through the planar waveguide is coupled out of the waveguide by the further grating. The outcoupled light is used for adjustment of the coupling of coherent light of predetermined wavelength into the planar waveguide. The coherent light propagates through the planar waveguide under total reflection with an evanescent field of the coherent light propagating along the outer surface of the planar waveguide. The depth of penetration of the evanescent field into the medium of lower refractive index at the outer surface of the planar waveguide is in the order of magnitude of a fraction of the wavelength of the coherent light propagating through the planar waveguide. The evanescent field excites the fluorescent tags of the labelled target samples bound to the binding sites arranged on the surface of the planar waveguide. Due to the very small penetration of the evanescent field into the optically thinner medium at the outer surface of the planar waveguide, only the labelled samples bound to the binding sites immobilized on the outer surface of the planar waveguide are excited. The fluorescent light emitted by these tags is then detected with the aid of a CCD camera.

While it is principally possible to detect the binding affinities using fluorescent labels, this technique is disadvantageous in that the detected signal is produced by the labels rather than by the binding partners themselves. In addition, labelling the target samples requires additional working steps. Moreover, labelled target samples are comparatively expensive. Another disadvantage is the falsification of the results caused by steric hindrance of the fluorescent labels at the target sample which might interfere with the binding of the target samples to the capture molecules. Further disadvantages are the falsification of the results due to photobleaching of the labels or quenching effects.

It is an object of the present invention to provide a device for use in the detection of binding affinities of a target sample as well as a system capable of detecting such binding affinities which overcome or at least greatly reduce the disadvantages of the prior art sensor described above.

In accordance with the invention, this object is achieved by a device for use in the detection of binding affinities. The device comprises a planar waveguide arranged on a substrate, and further comprises an optical coupler of a predetermined length for coupling coherent light of a predetermined wavelength into the planar waveguide such that a parallel beam of coherent light propagates through the planar waveguide with an evanescent field of the coherent light propagating along an outer surface of the planar waveguide. The outer surface of the planar waveguide comprises binding sites thereon capable of binding target samples to the binding sites such that light of the evanescent field is diffracted by target samples bound to the binding sites. The binding sites are arranged along a plurality of predetermined straight lines running parallel to one another with a constant distance between adjacent straight lines. The predetermined straight lines are arranged at an angle β relative to the direction of propagation of the evanescent field such that the coherent light diffracted by the target samples bound to the binding sites impinges under a diffraction angle α relative to the straight lines onto a further optical coupler arranged in a portion of the planar waveguide outside the beam of coherent light propagating through the planar waveguide. The further optical coupler couples the diffracted coherent light out of the planar waveguide such as to interfere at a predetermined detection location with a difference in optical path length which is an integer multiple of the predetermined wavelength. Technically, the term "diffracted" describes the interference of the coherent light of the evanescent field which already has interacted with target samples bound to the binding sites. The diffraction causes the coherent light propagating through the planar waveguide with an evanescent field at the outer surface to constructively interfere under predetermined directions within the planar waveguide.

The detection of binding affinities according to the invention is neither limited to specific types of target samples nor to any type of binding sites, but rather the binding characteristics of molecules, proteins, DNA etc. can be analysed with respect to any type of binding sites on the planar waveguide. The detection of binding affinities can be achieved in a label-free manner. Alternatively, diffraction enhancers (e.g. diffracting labels) which strongly scatter the light can be used to increase the detection sensitivity. Such diffraction enhancers can be a nanoparticle (alone or with a binder) or in another example a colloidal particle. Advantageously, the binding characteristic to be analysed can be of static type (for example, it can be analysed whether a target sample has or has not bound to the binding sites) or of dynamic type (for example, the dynamics of the binding process over time can be analysed). According to the invention the device comprises a planar waveguide on a substrate, the planar waveguide having a high refractive index relative to the medium on the outer surface forming the upper side of the planar waveguide. For example, the refractive index of the planar waveguide may be in the range of 1.6 to 2.8, whereas the refractive index of the medium at the surface of the planar waveguide is typically in the range of 1 to 1.6, in particular 1.33-1.4 for water or aqueous assay buffer and 1 for air. The effective refractive index N of the guided mode, the refractive index of the medium at the surface of the planar waveguide and the predetermined wavelength of the light determine the penetration depth (distance between the outer surface of the planar waveguide and the $1/e^2$ intensity descent of the evanescent field) of the evanescent field into the medium on the outer surface of the planar waveguide. The penetration depth is such that the evanescent field penetrating out of the outer surface of the planar waveguide is diffracted at the target samples bound to the binding sites arranged at the outer surface. In use, coherent light of a predetermined wavelength (which is preferably monochromatic) is coupled via an optical coupler into the planar waveguide such that a parallel beam of coherent light propagates through the planar waveguide with the evanescent field propagating along the outer surface. The parallel beam has a width corresponding to the predetermined length of the optical coupler which is in case of an optical grating for coupling coherent light into the planar waveguide the length of the lines defining the optical grating. The predetermined wavelength is not limited to specific values but is rather preferred to be in the range of visible light. The outer surface of the planar waveguide comprises binding sites thereon. Binding sites are locations on the outer surface of the planar waveguide to which a target sample may bind. For example, binding sites may comprise capture molecules which are immobilized on the outer surface of the planar waveguide, or may simply comprise activated locations on the outer surface of the planar waveguide which are capable of binding target samples to the activated locations, or may be embodied in any other manner suitable to bind target samples at the desired locations on the outer surface of the planar waveguide. In principle, binding sites being capable of binding target samples such that light of the evanescent field is diffracted by target samples bound to the binding sites. According to the invention, the binding sites are arranged along a plurality of predetermined straight lines. The arrangement of the binding sites "along the predetermined straight lines" represents the optimum case in which all binding sites are exactly arranged on the predetermined straight lines. Such optimal arrangement of the binding sites results in a maximum signal at the detection location. It is obvious to the person skilled in the art that in practice the arrangement of the binding sites can deviate to some extent from such optimum arrangement without losing a detectable signal in the detection location. For example, the deviation may be caused by the respective method for arranging the binding sites on the outer surface of the planar waveguide, as will be explained in detail below. The straight lines are such that light diffracted thereto constructively interferes in a maximum of high intensity within the planar waveguide. The predetermined straight lines run parallel to one another with a constant distance between adjacent straight lines. Preferred constant distances between adjacent predetermined straight lines are of the order of more than 100 nm. For the distance between adjacent predetermined lines a range of about 100 nm to about 1000 nm, in particular between 300 nm-600 nm is preferred. The mentioned ranges allow the use of visible, near infrared and soft UV light of which the wavelength ranges from 350 nm to 1500 nm so that the diffracted light can be detected by standard optical means. The predetermined straight lines are arranged at an angle $\beta$ in the range of 10° to 70° relative to the direction of propagation of the evanescent field. The direction of propagation is defined as starting from the optical coupler and extending in the direction in which the coherent light is coupled into the planar waveguide which is usually close to perpendicular to the lines of the optical grating which form the optical coupler. The coherent light diffracted by the target samples bound to the binding sites impinges onto the further optical coupler under the diffraction angle $\alpha$ relative to the straight lines. The diffraction angle under which the light constructively interferes by an integer multiple of the predetermined wavelength depends on the constant distance between adjacent predetermined straight lines taking into account the predetermined wavelength and the refractive indices of the substrate, the planar waveguide and of the medium at the outer surface of the waveguide at this wavelength. Since the light of the evanescent field propagating along the outer surface of the planar waveguide is coherent as is the light propagating through the planar waveguide, the coherent light of the evanescent field is diffracted coherently by the diffraction centers formed by the target samples bound to the binding sites which are arranged on the different predetermined straight lines. The diffracted light at any location can be determined by adding the contributions from each of the individual diffraction centers. Advantageously, the internal diffraction of the light propagating through the planar waveguide is of a higher efficiency compared to the diffraction of the guided light out of the planar waveguide. Since the diffraction at the target samples bound to binding sites is usually rather weak, the diffraction within the plane of the planar waveguide provides an improved detection sensitivity which even allows detecting comparatively small numbers of diffraction centers. The further optical coupler onto which the diffracted light impinges can be a physical grating suitable to couple the light out of the planar waveguide. A further crucial point of the invention is that the further optical coupler is arranged in a portion of the planar waveguide outside the beam of coherent light propagating through the planar waveguide. This allows detecting the signal from the diffracted light without a background from the beam of coherent light propagating through the planar waveguide. Because of the signal detected in the detection location has less background signal, a better detection sensitivity is achieved which allows to detect a signal caused by less diffraction centers. A maximum of the diffracted light is located at the predetermined detection location because the further optical coupler is formed as a grating such that at the predetermined detection location, the optical path length of the light diffracted by the different lines of the grating differs by an integer multiple of the wavelength of the light. For a maximum signal at the detection location, the optical path length of the light from the optical coupler to the predetermined straight lines, from there to the further optical coupler and from there to the predetermined detection location is also a multiple integer of the predetermined wavelength. Thus the light diffracted by the target samples bound to the binding sites constructively interferes at a predetermined detection location. The requirement of constructive interference is met by the diffracted light which adds to the detectable signal in the detection location.

According to an advantageous aspect of the invention, the constant distance d between the adjacent straight lines is chosen such as to fulfill the Bragg condition $2Nd\sin(\alpha)=k\lambda$, wherein N is the effective refractive index of the guided mode in the planar waveguide, d is the distance between adjacent predetermined straight lines, $\alpha$ is the diffraction angle, k is the number of the intensity maximum and $\lambda$ is the vacuum wavelength of the propagating light. It is important to note that the distance between adjacent predetermined straight lines d at which constructive interference at a predetermined detection location occurs depends on the effective refractive index N which—in turn—depends on the refractive index of the medium at the outer surface of the waveguide. Advantageously, the distance between adjacent predetermined straight lines d is chosen to factor in the change in refractive index for different samples applied to the outer surface. A constant distance d between adjacent lines explicitly includes small changes in the distance between adjacent lines. Such gradient in the distance between adjacent lines over the plurality of predetermined lines allows fulfilling the Bragg condition in only a fraction of the plurality of predetermined lines.

According to another advantageous aspect of the invention, the predetermined straight lines are arranged at the angle $\beta$ in the range of 10°-70° relative to the direction of propagation of the evanescent field. The coherent light diffracted by the target samples bound to the binding sites impinges under the diffraction angle $\alpha$ (which equals $\beta$) relative to the straight lines onto the further optical coupler. Arranging the predetermined straight lines and the further optical coupler at fixed angles is of advantage for the preparation of the predetermined straight lines on the outer surface of the device, which have a fixed orientation thereon.

According to a further advantageous aspect of the invention, the further optical coupler comprises a plurality of grating lines. Each of the plurality of grating lines has a respective curvature and distance between adjacent grating lines so that the further optical coupler is capable of coupling the diffracted coherent light out of the planar waveguide such as to interfere at a predetermined detection location with a difference in optical path length which is an integer multiple of the predetermined wavelength. The plurality of grating lines may have a symmetry axis which extends relative to the predetermined straight lines under the diffraction angle $\alpha$. This symmetry perseveres to a plurality of grating lines in the further optical coupler with a symmetric curved grid-like structure of a decreasing distance between adjacent grating lines so that light of a single predetermined wavelength coupled out of the planar waveguide fulfills the condition that the difference in optical path length is a multiple integer of the single predetermined wavelength in the detection location. To arrange the symmetry axis under the diffraction angle allows the detection location to include the central axis of the circular formed optical grating.

According to a still further advantageous aspect of the invention, the plurality of predetermined straight lines is arranged in an effective zone on the planar waveguide. The effective zone has a width equivalent to the length of the optical coupler so that the entire effective zone is illuminated by the evanescent field of the coherent light coupled into the planar waveguide by the optical coupler. The beam propagating in the waveguide has a small angle of divergence so that the increase of beam-width compared to the other dimensions of the device is negligible. Thus the width of the effective zone can generally be chosen identical to the length of the optical coupler for illuminating the entire effective zone. In practice however, the width of the effective zone is smaller compared to the length of the optical coupler. As an example, the width of the effective zone is 310 μm while the length of the optical coupler is 400 μm.

According to another advantageous aspect of the invention, at least two pluralities of predetermined straight lines are arranged on the planar waveguide one after the other in the direction of propagation of the evanescent field. A respective further optical coupler is arranged relative to each plurality of predetermined straight lines such that the coherent light diffracted by the target samples bound to the binding sites arranged along the straight lines of the respective plurality of straight lines impinges under a diffraction angle $\alpha$ onto the respective further optical coupler. By arranging the pluralities of predetermined straight lines one after the other in the direction of propagation of the evanescent field, the evanescent field of the beam impinges onto (diffracts at) all pluralities of predetermined straight lines arranged in such manner so as to allow the simultaneous detection of binding affinities in a multitude of samples.

In a preferred alternative aspect of the invention, the at least two pluralities of predetermined straight lines each have the same constant distance d between adjacent straight lines. The same constant distance d between adjacent straight lines of each plurality of predetermined straight lines allows a redundant detection of binding affinities in a multitude of samples.

In a further preferred alternative aspect of the invention, the at least two pluralities of predetermined straight lines each have a different constant distance $d_{1 \ldots n}$ between adjacent straight lines. The different constant distance $d_{1 \ldots n}$ may cover a range of constant distances which corresponds to a range of detectable refractive indices in the medium at the outer surface of the waveguide. The range of detectable refractive indices allows detecting binding affinities for samples in media with different or unknown refractive indices. The refractive index in the samples that are brought into contact with the sensor surface might vary in the range of a few per cents due to different composition. In a preferred additional aspect of the invention, the constant distance $d_{1 \ldots n}$ between adjacent straight lines of adjacent pluralities of predetermined straight lines differs, in steps of 0.5 to 3 nm. Having pluralities of predetermined straight lines with a difference in constant distance $d_{1 \ldots n}$ which changes in equal steps allows to conveniently quantify binding affinities in samples of different or unknown refractive indices in the range of known detectable refractive indices. Constructive interference at a predetermined detection location occurs when the distance d of the plurality of predetermined straight lines matches the Bragg condition for the refractive index of the applied sample.

In a still further preferred alternative aspect of the invention, the at least two pluralities of predetermined straight lines include groups of pluralities of predetermined straight lines, each group having an equal constant distance d between adjacent straight lines. Different groups of pluralities of predetermined straight lines have a different constant distance $d_{1 \ldots n}$ between adjacent straight lines. Having groups of equal constant distance d between adjacent straight lines combines the advantages discussed for the other alternatives so as to allow the redundant detection of binding affinities as well as to detect binding affinities for samples in media with different or unknown refractive indices in the range of known detectable refractive indices.

In a still further preferred aspect of the invention, the optical coupler comprises at least two separate portions for coupling coherent light of the predetermined wavelength into the planar waveguide. Each separate portion has a predetermined length and is separated by a predetermined spacing towards the other separate portion such that at least two parallel beams of coherent light propagate through the planar waveguide separated by the predetermined spacing. The separate portions of the optical coupler allow arranging one or more pluralities of predetermined straight lines in the direction of propagation of each beam coupled via the respective separate portion into the planar waveguide. By separating the parallel beams coupled to the waveguide with a predetermined spacing in between causes a portion of the planar waveguide outside the parallel beams of coherent light. The further optical coupler arranged in said portion improves the detected signal by reducing the background light in the detection location. In an example for the further optical coupler having a size of 400 µm, the predetermined spacing is chosen to be 600 µm.

According to an advantageous aspect of the invention, the binding sites comprise capture molecules attached to the outer surface of the planar waveguide along the predetermined straight lines only. The capture molecules are capable of binding the target samples. Two embodiments are particularly envisaged of how the binding sites can be arranged along the plurality of predetermined straight lines. According to a first embodiment, the binding sites comprise capture molecules attached to the surface of the planar waveguide along the predetermined lines only. These capture molecules are capable of binding the target samples and are immobilized on the outer surface of the planar waveguide (although, as mentioned above, the binding sites can be formed by the activated surface of the planar waveguide itself). Immobilizing the capture molecules on the outer surface of the planar waveguide along the predetermined lines can generally be performed by any suitable method, for example it may be performed using photolithographic methods using a lithographic mask with straight lines. It goes without saying, that the arrangement of the binding sites along the predetermined straight lines is to be understood in any embodiment of the invention in a sense that the majority of the binding sites—in the instant embodiment the capture molecules—are located along the predetermined straight lines and does explicitly include that some binding sites are arranged at locations different therefrom.

According to the second embodiment, the binding sites comprise capture molecules capable of binding the target samples, the capture molecules capable of binding the target samples being arranged along the predetermined straight lines by immobilization of the capture molecules capable of binding the target samples onto the outer surface of the planar waveguide and by deactivation those capture molecules which are not arranged along the predetermined straight lines. The term "deactivation" in this respect refers to any suitable method for changing the binding capability of the capture molecules before or after their immobilization on the outer surface of the planar waveguide. The deactivation can be achieved, for example, by exposing the capture molecules to UV light in order to achieve that they are no longer capable of binding target samples. The deactivation of the capture molecules immobilized between the predetermined straight lines can be achieved, for example, by an alteration of the binding region of the capture molecule. According to this embodiment of the invention, the capture molecules can be applied uniformly or statistically uniformly onto the outer surface of the planar waveguide. After deactivation of capture molecules which are arranged between the predetermined straight lines only the capture molecules arranged along the predetermined straight lines (these have not been deactivated) are capable of binding a target sample. Nevertheless, the deactivated capture molecules remain immobilized on the outer surface of the planar waveguide.

This embodiment has the additional advantage that the contribution of the signal generated by the light diffracted by target molecules bound to capture molecules to the overall signal at the detection location is increased. Generally, the difference between the signals of the light diffracted by small target molecules bound to the captures molecules and the light diffracted by the capture molecules without any target molecules bound thereto is small compared to the light diffracted by the capture molecules alone. Assuming that the diffraction properties of the capture molecules arranged along the predetermined straight lines (which have not been deactivated) and of the deactivated capture molecules arranged between the predetermined straight lines are nearly identical and further assuming that the capture molecules are homogeneously distributed over the outer surface of the planar waveguide, then ideally no signal is produced at the detection location after the capture molecules have been immobilized on the outer surface of the planar waveguide and after the capture molecules arranged between the predetermined straight lines have been deactivated. In practice, however, deactivation of the capture molecules slightly changes the diffraction properties of the capture molecules, so that it may not be ideal to deactivate all of the capture molecules which are arranged between the predetermined straight lines. Instead, only the vast majority of the capture molecules arranged between the predetermined straight lines may be deactivated. Deactivation of the capture molecules is performed to an extent such that the overall signal at the detection location produced by those capture molecules arranged along the predetermined straight lines and by those deactivated and the non-deactivated capture molecules arranged between the predetermined straight lines is at a minimum, and is preferably zero. Assuming that the signal so obtained at the detection location can be reduced to zero, this means, that after adding the target samples the signal produced at the detection location only results from target samples bound to the capture molecules. In case no target samples are bound to the capture molecules, the signal at the detection location remains zero. This increases the sensitivity of the detector for the signal generated by the light diffracted by the target molecules bound to the capture molecules at the detection location.

Another aspect of the invention relates to a system for the detection of binding affinities comprising a device according to any one of the preceding claims, and further comprising a light source for emitting coherent light of a predetermined wavelength. The light source and the device are arranged relative to one another such that the coherent light emitted by the light source is coupled into the planar waveguide via the optical coupler.

According to an additional aspect of the invention, the light source and the device are arranged adjustable relative to each other for changing the incoupling angle under which the coherent light emitted by the light source is coupled via the optical coupler into the planar waveguide. The light source emits coherent light of a predetermined wavelength, preferentially in the visible, near infrared or soft UV spectral range with a (tunable) wavelength in the range from 350 nm to 1500 nm.

According to a further aspect of the invention, the light source is tunable to emit coherent light of predetermined wavelength with a tuning range of about 1 to 5 nm. The tuning range of the light source allows arranging the light source and the device at a fixed incoupling angle. The light emitted by the tunable light source is coupled via an optical coupler (e.g. optical grating) into the planar waveguide when the wavelength of the emitted light in the tuning range matches the wavelength at which coupling occurs at the fixed incoupling angle.

The tunable light source can be used for a second advantageous mode of operation of the device in a system for the detection of binding affinities. The Bragg condition describing the maximum intensity of constructive interference relates the distance between adjacent predetermined straight lines, the angle under which the evanescent field is diffracted at the target samples bound to the binding sites which are arranged along the predetermined straight lines, the wavelength of the light propagating through the planar waveguide and the effective refractive index N of the guided mode. Considering samples of which the refractive index is not exactly known, the tunable light source allows to vary the wavelength at which coupling occurs such that the Bragg condition for the maximum intensity of constructive interference is fulfilled (even for a fixed distance between adjacent lines and a fixed diffraction angle relative to the predetermined lines). The variation of both, the wavelength of the tunable light source and the incoupling angle (under which the light is coupled via the optical coupler into the waveguide) allows to adjust the wavelength at which coupling into the waveguide occurs to the wavelength which fulfills the Bragg condition for a fixed distance between adjacent predetermined straight lines.

Further advantageous aspects of the invention become apparent from the following description of an embodiment of the device with reference to the accompanying drawings in which.

Figure 1:
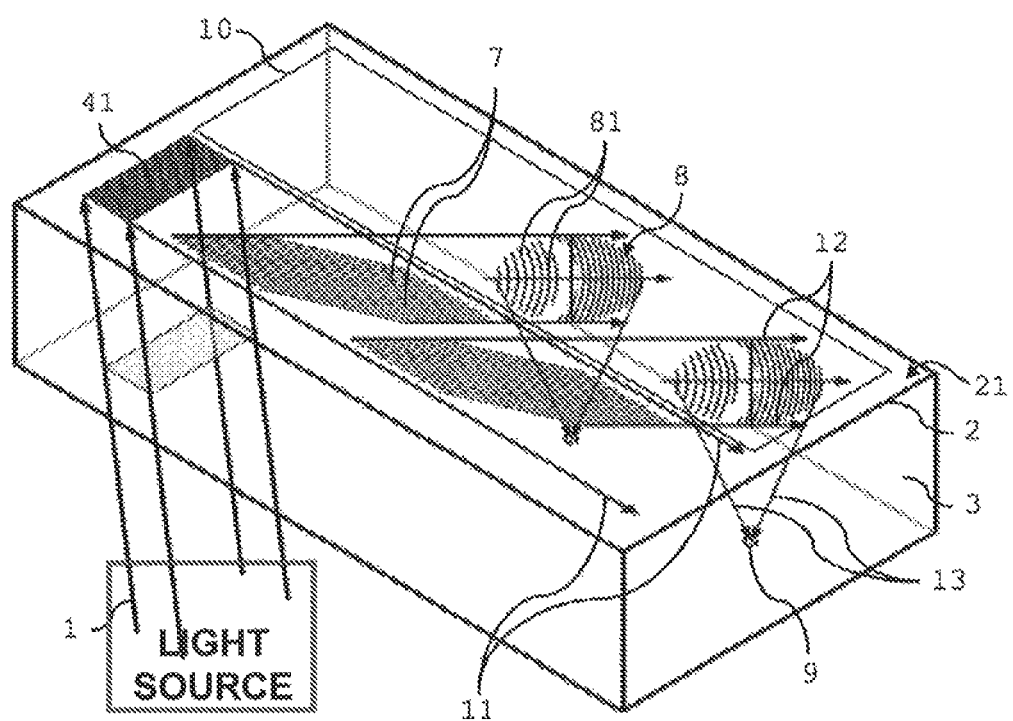
FIG. 1 shows a perspective view of a first embodiment of the device according to the invention.

FIG. 1 shows a perspective view of an embodiment of the device for use in the detection of binding affinities. Structurally, the device comprises a substrate 3, a plurality of predetermined straight lines 7 (each of the shown lines represent a multiplicity of lines) arranged on an outer surface 21 of a planar waveguide 2, an optical coupler 41, a detection location and a further optical coupler 8. It is further shown that according to the working principle of the device, the coherent light 1 is coupled into the planar waveguide 2 so as to propagate with an evanescent field 11 (represented by parallel arrows) which is diffracted so that diffracted coherent light 12 (represented by parallel arrows) propagates under an angle relative to the predetermined lines to be coupled out of the planar waveguide 2 such that coupled light 13 coupled out of the planar waveguide 2 interferes in the detection location 9.

In the shown example, the planar waveguide 2 is arranged on the substrate 3 which both allow visible coherent light to propagate therethrough. Since the planar waveguide 2 has a thickness in the range of some ten nanometers to some hundred nanometers it is drawn together with the line of the top surface from substrate 3. The coherent light 1 provided by a light source has a predetermined wavelength. In practice, the predetermined wavelength is not limited to specific values for the wavelength but rather is to be chosen inter alia according to the effective refractive index of the guided mode as well as to the size, position and geometry of the optical coupler 41, the predetermined lines 7 and the further optical coupler 8. For coupling the coherent light 1 of a predetermined wavelength into the planar waveguide 2, the optical coupler 41 employs in the shown example a grating with straight lines of a predetermined length so as to allow coherent coupling of the coherent light 1 under a predetermined coupling angle into the planar waveguide 2. Because of the predetermined length of the coupler 41 a parallel beam of coherent light having a width according to the length of the optical coupler 41 propagates through the planar waveguide 2. The parallel beam of coherent light has an evanescent field 11 of a characteristic penetration depth. The penetration depth of the evanescent field 11 into the medium on the outer surface 21 of the planar waveguide 2 (distance between the outer surface 21 of the planar waveguide 2 and the $1/e^2$ intensity descent of the evanescent field 11) depends on the effective refractive index N of the guided mode, on the refractive index of the medium at the surface of the planar waveguide and on the wavelength .lamda. of the light. The light of the evanescent field 11 is diffracted by target samples (not shown in FIG. 1) bound to the binding sites (not shown in FIG. 1). In principle, the binding sites are arranged along the plurality of predetermined straight lines 7 which run parallel to one another with a constant distance between adjacent straight lines. The predetermined straight lines 7 are arranged on the outer surface 21 of the planar waveguide 2 at an angle relative to the direction of propagation of the evanescent field 11. The light of the evanescent field 11 is diffracted so as to impinge under a diffraction angle relative to the straight lines onto a further optical coupler 8 formed in the planar waveguide 2. The diffracted light interferes in the further optical coupler 8 with a difference in optical path length of a multiple integer of the predetermined wavelength. Advantageously, the internal diffraction of the light propagating through the planar waveguide 2 is of a higher efficiency compared to the diffraction of the guided light out of the planar waveguide 2. This provides a sufficient detection sensitivity which allows detecting comparatively small numbers of diffraction centers. In theory, there might be other diffraction angles relative to the straight lines having a maximum intensity of the diffracted light so that the further optical coupler 8 can be arranged at other diffraction angles, as well. A further advantage of the invention can be seen from FIG. 1 with respect to the arrangement of the further optical coupler 8. The further optical coupler 8 and thus the detection location 9 are arranged on the planar waveguide 2 and oriented relative to each other such that no light of the beam propagating through the planar waveguide 2 is detected. Thus, the further optical coupler 8 is arranged in a portion 10 of the planar waveguide 2 outside the beam of coherent light propagating through the planar waveguide 2 starting from the optical coupler 41. This allows detecting the signal from the diffracted light without a background from the beam of coherent light propagating through the planar waveguide. A still further advantage relates to the signal detected in the detection location 9 having less background signal because of the location of the further optical coupler 8 in the portion 10. Thus, a better detection sensitivity is achieved which allows to detect a signal caused by less diffraction centers. The further optical coupler 8 is shown to be a phase grating lens oriented with the axis of symmetry in the direction of the diffraction angle. The phase grating lens exemplifies any optical means to couple the diffracted coherent light 12 out of the planar waveguide 2 while focusing it in the detection location 9 with a sufficient intensity for the detection of binding affinities.

FIGS. 2-6, respectively, are plan views of the outer surface 21 of the planar waveguide 2 from FIG. 1 which already describes the planar waveguide 2, the optical coupler 41, the further optical coupler 8 and the plurality of predetermined lines 7 arranged on the outer surface 21 of the planar waveguide 2.

Figure 2:
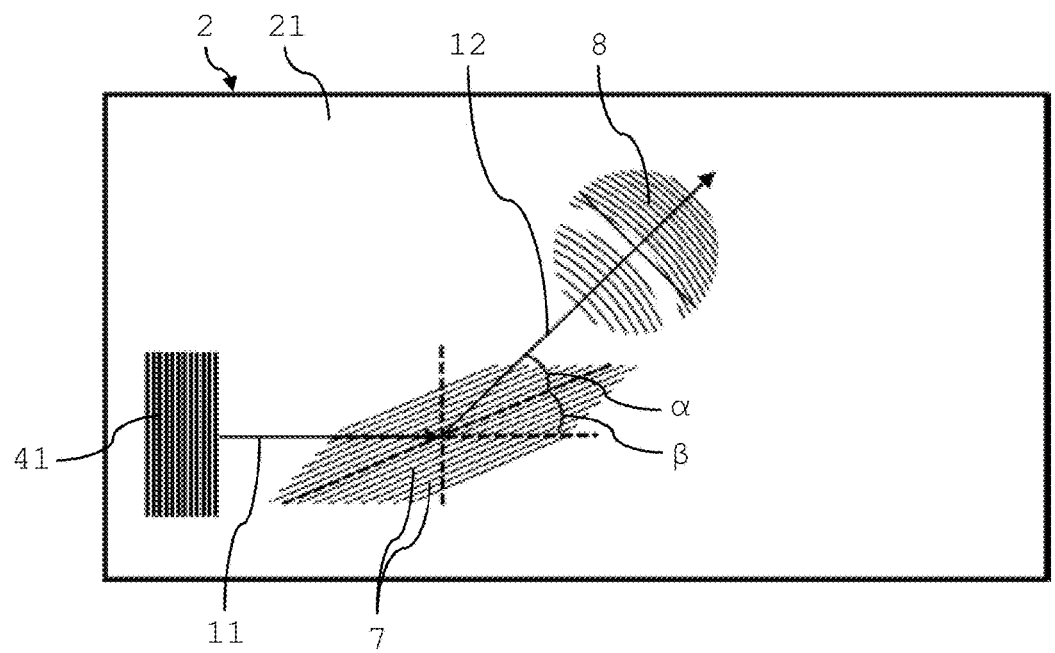
FIG. 2 shows a plan view of the planar waveguide of the device of FIG. 1 illustrating different angles according to the invention.

In FIG. 2 the angle α relative to the predetermined straight lines 7 and the angle β relative to the direction of propagation of the evanescent field 11 are illustrated. In the present embodiment the angle β is 22.5° and the angle α is 22.5°. The fixed angles are obviously of advantage for the preparation of the device. The evanescent field 11 (represented by an arrow starting from the optical coupler 41 and ending in the center of the predetermined straight lines 7) propagating along the outer surface 21 of the planar waveguide 2 diffracts on target samples (not shown) bound to binding sites (not shown). The diffracted coherent light 12 (represented by an arrow starting from the center of the predetermined straight lines 7 and propagating along the symmetry axis of the further optical coupler 8) constructively interferes such as to impinge under the angle α of 22.5° onto the further optical coupler 8. The angle α is according to the Bragg condition $2Nd \sin(\alpha) = k\lambda$ dependent from the distance d between adjacent predetermined straight lines 7 and from the predetermined wavelength λ and can be varied to fulfill the Bragg condition. N is the effective refractive index of the guided mode in the planar waveguide and λ is the vacuum wavelength of the light propagating through the planar waveguide 2.

Figure 3:
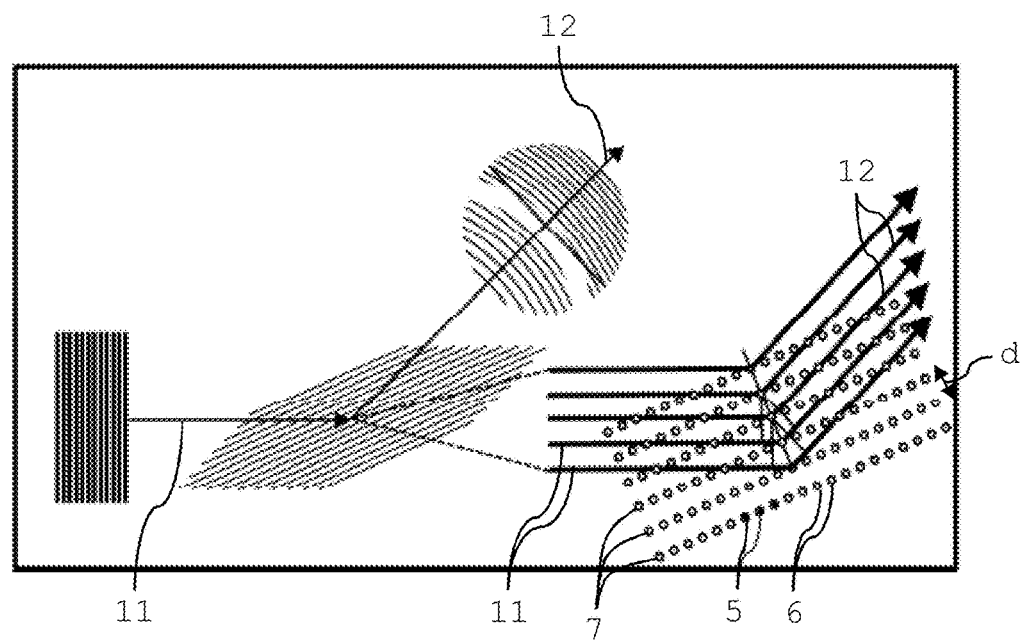
FIG. 3 shows a plan view of the planar waveguide of the device of FIG. 1 illustrating the arrangement of the binding sites.

A plan view of the planar waveguide 2 of the device of FIG. 1 with an exaggerated illustration of the binding sites 5 arranged along predetermined straight lines 7 is provided in FIG. 3. In the exaggerated illustration, the light of the evanescent field 11 is represented by parallel arrows approaching the predetermined straight lines 7, which are arranged under a known angle β thereto. The predetermined straight lines 7 are arranged parallel to one another with a constant distance d. The diffracted coherent light 12 diffracted on the target samples 6 bound to the binding sites 5 arranged along the predetermined straight lines 7 has for predetermined angles a difference in optical path length which is a multiple integer of the wavelength. The diffracted coherent light 12 has for those predetermined angles a maximum intensity. The described diffraction angle is the first angle under which such a maximum in intensity occurs. In fact this is the well-known drawing depicting the principle of Bragg diffraction in which the light is diffracted at "crystal structures" to constructively interfere in certain directions. This illustration is not correct insofar as the binding sites 5 and in this way the target samples 6 bound to the binding sites 5 are not arranged along the predetermined straight lines 7 in the shown regular order. The arrangement of those deviate to some extend in both, along those lines and perpendicular to those lines without losing the intensity maximum of the diffracted coherent light 12.

Figure 4:
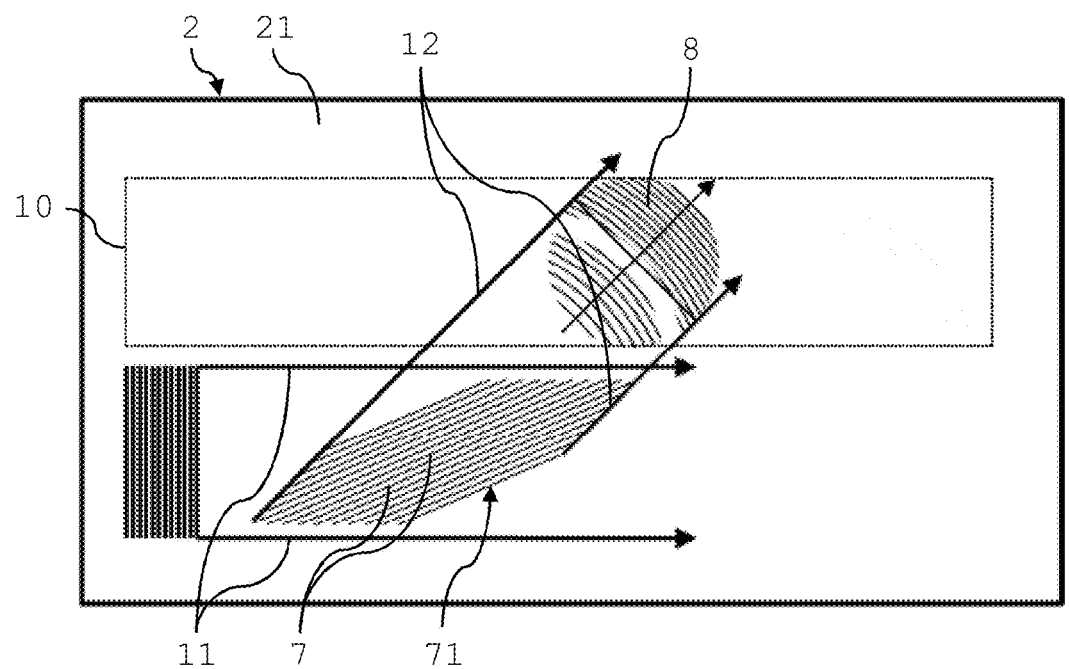
FIG. 4 shows a plan view of the planar waveguide of the device of FIG. 1 illustrating an effective zone.

In FIG. 4 the arrangement of the predetermined straight lines 7 in an effective zone 71 on the planar waveguide 2 is explanatorily depicted. The construction of the effective zone 71 is shown with respect to the coherent light propagating through the planar waveguide 2. Assuming a uniform density of diffraction centers in the effective zone 71, in principle, the bigger the area of the effective zone 71, the more diffraction centers will contribute to the diffracted coherent light 12. The area of the effective zone 71 is primarily chosen in dependence on the strength of the detected signal to be suitable for detecting the binding affinities. Since the length of the optical coupler 41 is fixed, the width of the effective zone 71 is fixed to be equivalent thereto. This allows illuminating the entire effective zone 71 by the evanescent field 11, as shown by the parallel arrows laterally confining the width of the effective zone 71. The length of the effective zone 71 is such that at one hand the diffracted coherent light 12 impinges entirely on the further optical coupler 8 while on the other hand the further optical coupler 8 is only illuminated by the diffracted coherent light 12 from diffraction centers in the effective zone 11. The lateral separation of diffracted coherent light 12 from the evanescent field 11 restricts the light impinging on the further optical coupler 8 to diffracted coherent light 12 from diffraction centers in the effective zone 71 and avoids additional background light in the region 10 through which—apart from the diffracted light 12—no other light propagates.

Figure 5:
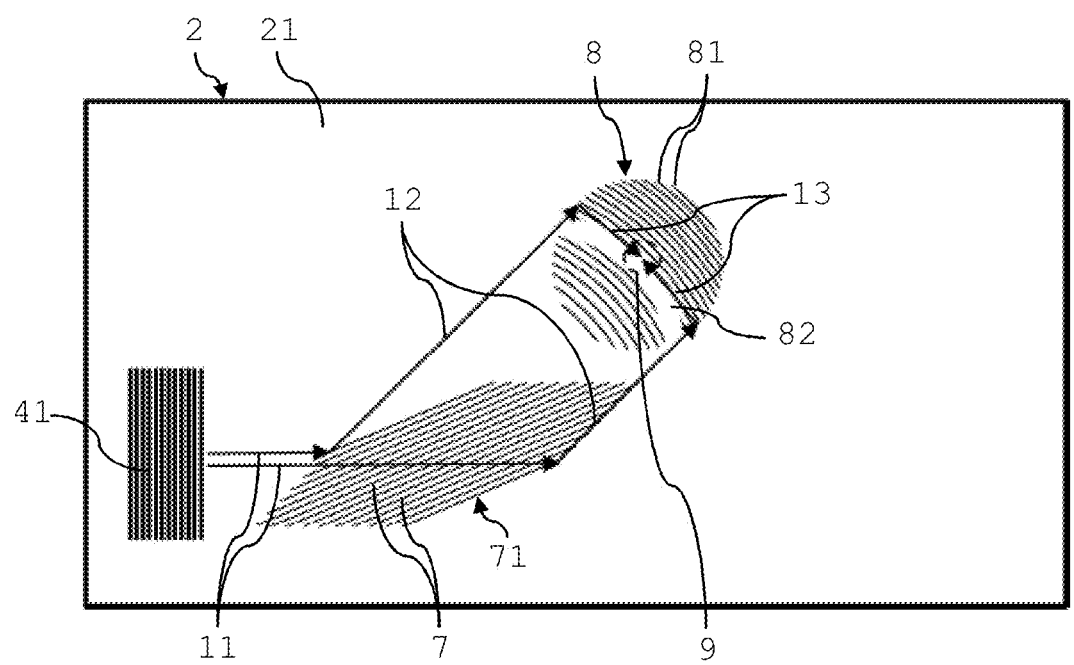
FIG. 5 shows a plan view of the planar waveguide of the device of FIG. 1 illustrating different optical paths.

In FIG. 5 two examples for different optical paths of light are illustrated by the arrows for the evanescent field 11, the arrows for diffracted coherent light 12 as well as for the light 13 interfering in the detection location 9. In principle, a multiplicity of parallel beams start at the optical coupler 41 to diffract over the entire area of the effective zone 71 in which the predetermined straight lines 7 are arranged. The diffracted coherent light 12 propagates towards the further optical coupler 8 with difference in optical path of a multiple integer of the predetermined wavelength. The diffracted coherent light 12 impinges on the further optical coupler 8 such as to be coupled out of the planar waveguide 2. The further optical coupler 8 is depicted as optical grating with a plurality of grating lines 81. The grating lines 81 are formed such that the diffracted coherent light 12 impinging thereon is coupled out of the planar waveguide 2 and is focused into the detection location 9. For focusing the light 13 coupled out of the planar waveguide into the detection location 9, each of the plurality of grating lines 81 has a respective curvature and the lines are arranged with a decreasing distance between adjacent grating lines 81 in the direction of propagation of the diffracted coherent light 12. This allows diffraction of light of a predetermined wavelength "ideally" into a single point of focus with a difference in optical path length which is a multiple integer of the predetermined wavelength. A blank section 82 is formed in the further optical coupler 8 to avoid a 2nd order Bragg reflection, or similar optical effects, which potentially decrease the overall intensity of the detected signal.

Figure 6:
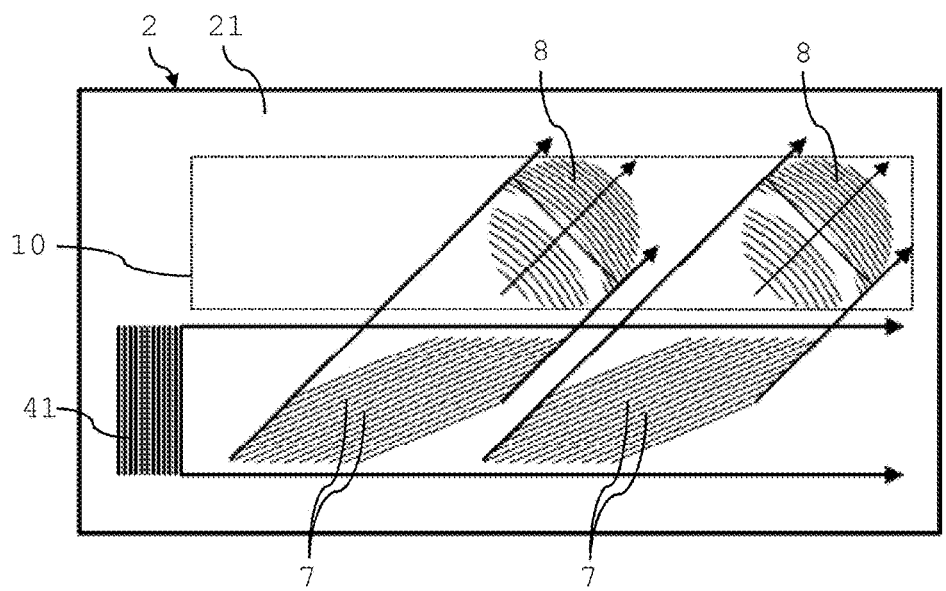
FIG. 6 shows a plan view of the planar waveguide of the device of FIG. 1 having two pluralities of predetermined straight lines.

One advantageous aspect of the present invention is shown in FIG. 6, wherein the planar waveguide 2 of the device of FIG. 1 comprises two pluralities of predetermined straight lines 7. The two pluralities of predetermined straight lines 7 have a different distance between adjacent predetermined straight lines 7. In general, the different distance between adjacent predetermined straight lines 7 allows the detection of binding affinities for samples having a different refractive index under the same "fixed" diffraction angle. Each different refractive index of the sample causes a different effective refractive index for the light propagating through the planar waveguide 2. Generally, the effective refractive index of the guided mode in the planar waveguide depends on the thickness and the refractive index of the planar waveguide 2, the refractive index of the substrate, the refractive index of a medium on the outer surface 21 of the planar waveguide 2 and the polarization of the guided mode. Thus, the evanescent field 11 of the light propagating through the planar waveguide 2 has different specific optical path length between adjacent lines for different samples on the waveguide. In practice, the refractive index of the medium on the outer surface 21 of the planar waveguide 2 is not exactly known. Advantageously, the plurality of predetermined straight lines 7 with different distances allow to detect a signal for an unknown refractive index in a range of known detectable refractive indices which might vary in the second or third decimal of the refractive index from sample to sample. For the detection of binding affinities it is sufficient if a single plurality of predetermined straight lines 7 shows a detectable signal. As shown, the at least two pluralities of predetermined straight lines 7 are arranged on the planar waveguide 2 in the direction of propagation of the evanescent field 11. The coherent light 12 coupled into the planar waveguide 2 is diffracted by the target samples 6 bound to the binding sites of each plurality of predetermined straight lines 7. A further optical coupler 8 is provided at each plurality of predetermined straight lines 7 for light impinging under a diffraction angle relative to the straight lines in a region 10 outside the beam of coherent light.

Figure 7:
FIG. 7 shows three pluralities of predetermined lines having a difference in constant distance d between adjacent predetermined straight lines.

FIG. 7 refers again to the idea to arrange at least two pluralities of predetermined straight lines 7 at the planar waveguide 2. This is illustrated by the arrangement of three pluralities of predetermined lines 7 with the plurality on the left side marked as having a first constant distance $d_{1 \ldots 24}$ between adjacent straight lines 7 out of a number of 24 constant distances. This refers to the idea that 24 pluralities of predetermined straight lines 7 are arranged each having a different constant distance d between adjacent straight lines. As an example, the distance $d_1$ between adjacent predetermined lines is 446 nm and the distance $d_2$ between adjacent predetermined lines is 447 nm. 24 pluralities of predetermined straight lines is an arbitrarily chosen number which provides in the present example a range of 24 different distances between 446 nm to 469 nm in steps of 1 nm. The mentioned steps provide a range sufficient to cover the expected variation of effective refractive indices in the second or third decimal (corresponding to an effective refractive index variation in the percent to per mille range).

Figure 8:
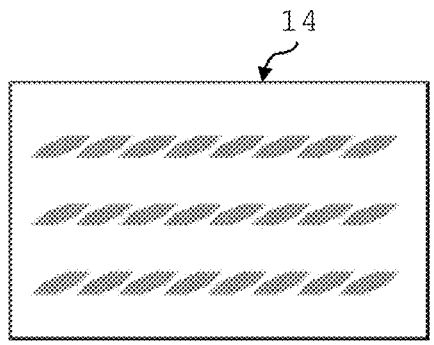
FIG. 8 shows a plan view of a mask to be used for preparation of a device according to a second embodiment of the invention having the pattern of 24 pluralities of predetermined straight lines thereon.
Figure 9:
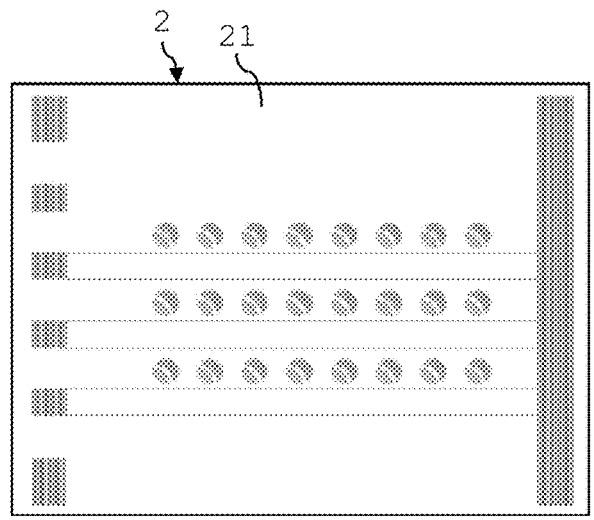
FIG. 9 shows a plan view of a non-prepared device according to the second embodiment of the invention to be prepared with the mask of FIG. 8.
Figure 10:
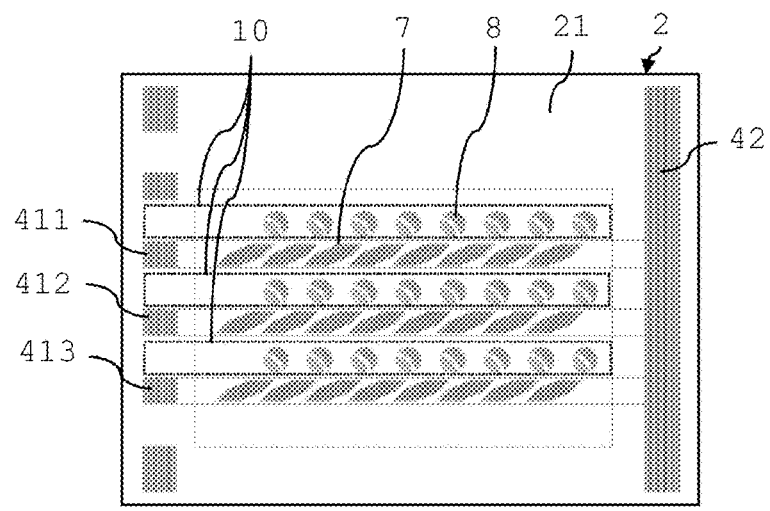
FIG. 10 shows a plan view of the prepared device according to the second embodiment of the invention which is the device of FIG. 9 ready for use in the detection of binding affinities.

A second embodiment of the invention is provided in the device shown in FIGS. 9 and 10, which depict the device before preparation, as well as, when readily prepared for use. Said device is prepared with the mask 14 shown in FIG. 8.

FIG. 8 shows the mask 14 for use in a photolithographic method for arranging the binding sites 5 to the outer surface 21 of the planar waveguide 2 along the predetermined straight lines 7. Such a mask 14 comprises a pattern thereon suitable to transfer predetermined straight lines 7 on the outer surface 21. The pattern is used in photolithographic procedures to attach the binding sites in predetermined straight lines 7 on the outer surface 21 of the planar waveguide 2. The not yet prepared device is shown in FIG. 9. Photolithographic methods exemplify any suitable method for arranging the predetermined straight lines 7 at the outer surface 21 of the planar waveguide 2. In general every method known in the art suitable to structure binding sites on the nanometer to micrometer scale can be employed to arrange the binding sites thereon. In FIG. 10 the prepared device is shown with 24 pluralities of predetermined straight lines 7. The 24 pluralities of predetermined straight lines 7 are arranged in a line with respect to one of the three separate portions 411, 412, 413 so that the coherent light coupled via each of said separate portions diffracts on eight pluralities of predetermined straight lines 7 arranged one after the other. The 24 pluralities of predetermined straight lines 7 are arranged in three parallel rows having a distance in between which forms a portion 10 of the planar waveguide 2 outside the parallel beams of coherent light propagating through the planar waveguide. The optical coupler 41 comprises three separate portions 411, 412, 413 for coupling three parallel beams of coherent light into the planar waveguide 2. The three separate portions 411, 412, 413 forming the optical coupler are arranged in a row and being laterally spaced by a predetermined distance from the adjacent separate portion. Thus the parallel beams of coherent light propagate through the planar waveguide 2 separated by this predetermined distance. Each separate portion 411, 412, 413 has a predetermined length equal to the width of the plurality of predetermined straight lines 7 arranged in a single row of pluralities. Each separate portion 411, 412, 413 couples a beam of coherent light into the planar waveguide. In between are three portions 10 on the outer surface 21 of the planar waveguide 2 which are outside the beams of coherent light. The portions 10 are used to arrange the further optical coupler 8 respectively to each plurality of predetermined straight lines 7. The coherent light which is not diffracted by the target samples bound to the binding sites arranged along the predetermined straight lines 7 propagates through the planar waveguide to the still further optical coupler 42 for coupling out the light propagating through the planar waveguide 2 which is not diffracted at the target samples bound to the binding sites arranged along the predetermined straight lines 7.

Figure 11:
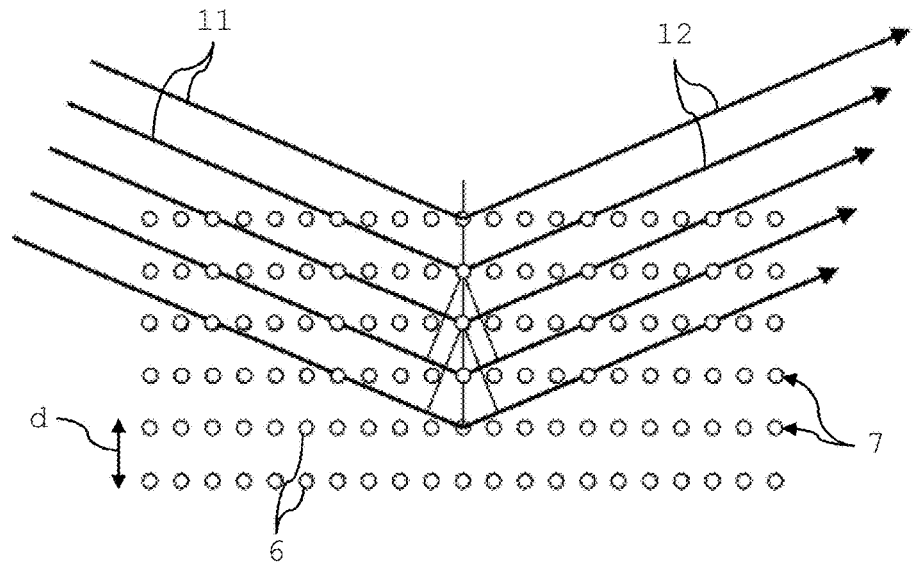
FIG. 11 shows a schematic illustration visualizing the difference in optical path length for the diffraction of the light of the evanescent field on target samples bound to binding sites arranged along the plurality of predetermined straight lines.
Figure 12:
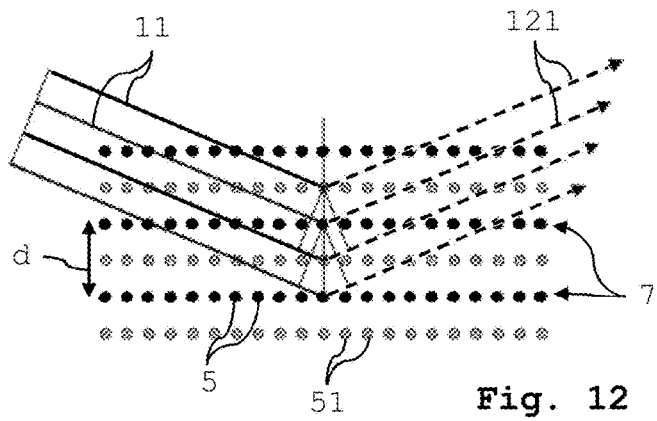
FIG. 12 shows the schematic illustration of FIG. 11 with binding sites comprising capture molecules along a plurality of predetermined straight lines and in between deactivated capture molecules for achieving a minimum background signal.
Figure 13:
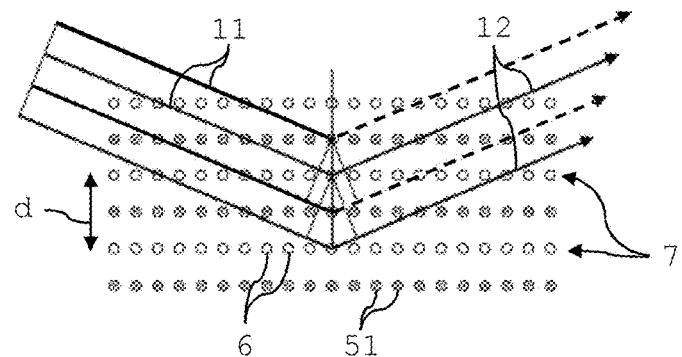
FIG. 13 shows the schematic illustration of FIG. 12 with the target samples applied to the capture molecules capable of binding.

FIG. 11, FIG. 12 and FIG. 13 illustrate examples for the diffraction of the light of the evanescent field 11. The light 11 is diffracted at the target samples 6 bound to the binding sites 5 arranged along predetermined lines 7 of a distance d so as to contribute to a maximum in a predetermined detection location. The shown illustrations are well known from the description of Bragg diffraction in "crystal structures". In principle, the Bragg condition $2Nd \sin(\alpha)=k\lambda$ describes the angles under which a maximum intensity of diffracted light can be detected. Due to the parallel arrangement of the predetermined straight lines 7 at a constant distance d between adjacent lines, the light of the evanescent field 11 diffracted on subsequent lines interferes under predetermined diffraction angles so as to have a difference in optical path length of a multiple integer of the predetermined wavelength of the light propagating through the planar waveguide 2. Thus, the shown parallel beams 12 of the diffracted light interfere at those diffraction angles so as to have a difference in optical path length of a integer multiple of the predetermined wavelength of the propagating light. The shown samples exemplify target samples 6 bound to binding sites without any precondition to the type of binding sites as well as the type of target samples 6. For the constructive interference it is crucial to arrange the binding sites to which the target samples may bind, or not, along the predetermined straight lines 7 so that the light constructively interferes under the prescribed conditions.

In FIG. 11, the binding sites comprise a single type of capture molecules. The detection of binding affinities tests the capability of capture molecules to bind target samples 6, or not, by actually observing the binding of the target samples 6 to the capture molecules. The capture molecules are in this first example attached to the outer surface of the planar waveguide to be arranged along the predetermined straight lines 7 only.

According to another example shown in FIG. 12 and FIG. 13, the capture molecules 5 capable of binding the target samples 6 being arranged along the predetermined straight lines 7 by arranging capture molecules 5 capable of binding the target samples 6 onto the entire outer surface of the planar waveguide and by deactivating those capture molecules 51 which are not arranged along the predetermined straight lines 7.

This is achieved by that the capture molecules are immobilised over the (entire) outer surface of the planar waveguide, so that there is no arrangement of the capture molecules along the plurality of predetermined lines 7 only. Thus, the light of the evanescent field 11 diffracted by the capture molecules 5 and the capture molecules 51 does not interfere at the further optical coupler in the manner described above for the diffracted coherent light 12.

Subsequently, the capture molecules 51 arranged between the predetermined lines 7 are deactivated so that no target samples 6 can bind to these deactivated capture molecules 51 anymore. As shown in FIG. 12, deactivation is performed such that after deactivation the overall signal at the further optical coupler (no target samples 6 have been added yet) produced by the deactivated capture molecules 51 and the capture molecules 5 capable of binding the target samples is set or adjusted to a tuned minimum signal (so as to destructively interfere) at the detection location, ideally to zero. The light 121 diffracted at the deactivated capture molecules 51 as well as at the capture molecules 5 has a difference in optical path length so as to add to a minimum in a predetermined detection location. The shown lines of capture molecules 5 and deactivated capture molecules 51 are "ideal" lines but provide a sufficient approximation since the light diffracted from capture molecules 5 and deactivated capture molecules 51 arranged other than (or in the proximity of) the plurality of predetermined "ideal" lines 7 in principle eliminates itself.

Alternatively, the minimum signal before the application of the target samples can be achieved by that capture molecules 5 and deactivated capture molecules 51 are subsequently applied so that in a first step the capture molecules 5 are applied to the outer surface of the planar waveguide along the plurality of predetermined straight lines 7 (comparable to FIG. 11). In a subsequent step, deactivated capture molecules 51 are applied in between the lines of the plurality of predetermined straight lines 7.

In the last step, the target samples are added to the outer surface of the planar waveguide. Since only the capture molecules arranged along the predetermined lines 7 are capable of binding the target samples 6, the target samples 6 bind to those capture molecules along the predetermined lines 7, as this is shown in FIG. 13. Due to the signal at the detection location caused by the deactivated capture molecules 51 and the capture molecules has been set or adjusted to a minimum before (see FIG. 12), the signal at the detection location is then mainly (or entirely, if the signal produced by deactivated capture molecules 51 and the capture molecules 5 has been reduced to zero before) caused by the light 12 which has been diffracted by the target samples 6 bound to the capture molecules arranged along the predetermined lines 7.

While the embodiments of the invention have been described with the aid of the drawings, various modifications and changes to the described embodiments are possible without departing from the general teaching underlying the invention. Therefore, the invention is not to be understood as being limited to the described embodiments, but rather the scope of protection is defined by the claims.

The invention claimed is:

1. A device for use in the detection of binding affinities, the device comprising:
    a substrate having a bottom surface, a top surface, two side surfaces and two end surfaces,
    a planar waveguide arranged on and in physical contact with the top surface of the substrate and having an inner surface in physical contact with the top surface of the substrate and an outer surface opposite the inner surface, the planar waveguide having a length dimension and a width dimension,
    an optical coupler in physical contact with the planar waveguide and having a first plurality of grating lines, the optical coupler having a width dimension in a direction of the width dimension of the planar waveguide, the optical coupler having a length dimension in a direction of the length dimension of the planar waveguide,
    a binding area positioned on the outer surface of the planar waveguide and in front of the optical coupler along the length dimension of the planar waveguide,
        the binding area comprising a plurality of binding sites arranged in straight lines at a first angle to the length dimension of the planar waveguide, the plurality of binding sites arranged in straight lines comprising capture molecules, and
        the binding area having a width dimension in the direction of a width dimension of the planar waveguide, the width dimension of the binding area being less than the width dimension of the optical coupler, and
    a further optical coupler in physical contact with the planar waveguide and spaced from the optical coupler and the binding area comprising the plurality of binding sites in the direction of the width dimension of the planar waveguide, the further optical coupler having a second plurality of grating lines at a second angle to the first angle along which the plurality of binding sites are arranged, the second plurality of grating lines having a respective curvature and being arranged with a decreasing distance between adjacent grating lines, the further optical coupler being arranged outside of the width dimension of the optical coupler but within the width dimension of the planar waveguide, wherein:

the optical coupler is configured to receive from a source a first coherent light beam of a predetermined wavelength and couple a second coherent light beam through the planar waveguide to the binding area comprising the plurality of binding sites, the capture molecules being capable of binding the target samples, the target samples configured to diffract the second coherent light beam and couple a third coherent light beam into the further optical coupler, and the further optical coupler being configured to couple a fourth coherent light beam out of the planar waveguide to interfere at a predetermined detection location with a difference in optical path length that is an integer multiple of the predetermined wavelength of the first coherent light beam.

2. The device according to claim 1, wherein the binding area comprising the plurality of binding sites arranged in straight lines is arranged in an effective zone on the planar waveguide, the effective zone having a width dimension equivalent to a predetermined length of the optical coupler so that the effective zone is illuminated by an evanescent field of the second coherent light beam.

3. The device according to claim 1, wherein at least two pluralities of the plurality of binding sites arranged in straight lines are arranged on the planar waveguide one after the other in the direction of the length dimension of the planar waveguide, with the further optical coupler being arranged relative to each plurality of binding sites arranged in straight lines such that the second coherent light beam that is diffracted by target samples bound to binding sites of the plurality of binding sites impinges under a diffraction angle ($\alpha$) onto the further optical coupler.

4. The device according to claim 3, wherein the at least two pluralities of the plurality of binding sites arranged in straight lines each have the same constant distance d between adjacent straight lines of the plurality of binding sites arranged in straight lines.

5. The device according to claim 3, wherein the at least two pluralities of the plurality of binding sites arranged in straight lines each have a different constant distance $d_1 \ldots n$ between adjacent straight lines of the plurality of binding sites arranged in straight lines.

6. The device according to claim 5, wherein the constant distance $d_1 \ldots n$ between adjacent straight lines of the plurality of binding sites arranged in straight lines differs in equal steps in the range of 0.5 nanometers to 10 nanometers.

7. The device according to claim 3, wherein the at least two pluralities of the plurality of binding sites arranged in straight lines include groups of binding sites arranged in pluralities of predetermined straight lines, each group having an equal constant distance d between adjacent straight lines of the group, and different groups of pluralities of predetermined straight lines having a different constant distance $d_1 \ldots n$ between adjacent straight lines of each group.

8. The device according to claim 1, wherein the optical coupler comprises at least two portions for coupling the first coherent light beam into the planar waveguide, each of the at least two portions having a predetermined length and being laterally spaced by a predetermined distance from an adjacent portion of the at least two portions of the optical coupler such that the second coherent light beam propagates through the planar waveguide separated by the predetermined distance.

9. A system comprising a device according to claim 1 and a light source for emitting coherent light of a predetermined wavelength, the light source and the device being arranged relative to one another such that the coherent light emitted by the light source is coupled into the planar waveguide via the optical coupler.

10. The system according to claim 9, wherein:

the light source and the device are arranged relative to each other such that the coherent light emitted from the light source impinges on the optical coupler under an incoupling angle under which the coherent light emitted by the light source is coupled via the optical coupler into the planar waveguide;

the light source and the device are adjustable relative to each other for changing the incoupling angle under which the coherent light emitted by the light source is coupled via the optical coupler into the planar waveguide, and the light source is tunable to emit light of a predetermined wavelength in a predetermined range.

11. The device according to claim 1, wherein a distance between adjacent grating lines of the first plurality of grating lines is between 100 nanometers and 1000 nanometers.

* * * * *